United States Patent [19]

Mirviss et al.

[11] Patent Number: 4,661,298

[45] Date of Patent: Apr. 28, 1987

[54] PROCESS FOR THE FORMATION OF PHOSPHONOALKYLATED AMINO ACIDS

[75] Inventors: Stanley B. Mirviss, Stamford, Conn.; Edward D. Weil, Hastings-on-Hudson, N.Y.

[73] Assignee: Stauffer Chemical Company, Westport, Conn.

[21] Appl. No.: 528,283

[22] Filed: Aug. 31, 1983

[51] Int. Cl.⁴ .............................................. C07F 9/38
[52] U.S. Cl. ...................... 260/502.5 F; 260/502.5 E
[58] Field of Search ................... 260/502.5 F, 502.5 E

[56] References Cited

U.S. PATENT DOCUMENTS

| 2,599,807 | 6/1952 | Bersworth | 260/502.5 E |
| 2,609,390 | 9/1952 | Bersworth | 260/502.5 F |
| 2,841,611 | 7/1958 | Bersworth | 260/502.5 E |

FOREIGN PATENT DOCUMENTS 213853  5/1968  U.S.S.R. ....................... 260/502.5 E

Primary Examiner—J. E. Evans
Attorney, Agent, or Firm—Richard P. Fennelly

[57] ABSTRACT

The reaction of amino acids and a haloalkylphosphonic acid to form the corresponding phosphonoalkylated amino acid is promoted by use of a catalytically effective amount of a polyamine catalyst which contains a sufficiently high concentration of amine nitrogen atoms to promote the reaction.

9 Claims, No Drawings

PROCESS FOR THE FORMATION OF PHOSPHONOALKYLATED AMINO ACIDS

BACKGROUND OF THE INVENTION

1. Field of the Invention

The present invention relates to a process for the preparation of phosphonoalkylated amino acids.

2. Description of the Prior Art

Various processes have been described for the preparation of phosphonoalkylated amino acids. For example, in U.S. Pat. Nos. 3,799,758 and 3,977,860 to J. E. Franz, it is suggested that N-(phosphonomethyl)glycine (a known herbicidal compound) be prepared by reacting the amino acid (glycine) with chloromethylphosphonic acid under alkaline conditions.

SUMMARY OF THE INVENTION

It has now been discovered that the reaction of an amino acid with a haloalkylphosphonic acid to form the corresponding N-phosphonoalkylated amino acid can be enhanced by the use of a catalytically effective amount of a polyamine catalyst which contains a high enough concentration of amine nitrogen atoms to enhance the reaction.

DETAILED DESCRIPTION OF THE PRESENT INVENTION

The present invention relates to a catalyzed reaction between an amino acid and a haloalkylphosphonic acid.

The amino acid is of the formula

$$HO_2CRNH_2$$

where R is a substituted or unsubstituted alkylene moiety containing from about 1 to about 10 carbon atoms in its backbone. Representative substituents for the moiety R include alkyl (e.g., $C_1$ to $C_6$ alkyl), aryl, arylalkyl and a nitrogen heterocycle (e.g., derived from pyrrole, indole, imidazole, purine, pyridine, etc.). The substituents can be the same or different.

The halomethylphosphonic acid is of the formula

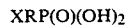

$$XRP(O)(OH)_2$$

where R is as defined above and X is either chlorine or bromine.

Preferably, R in both cases is methylene to yield N-(phosphonomethyl)glycine.

The reaction is conducted under alkaline conditions, e.g., a pH of 8.5–12.5, most preferably 9.5–10.5, in order to achieve the most advantageous yields. The molar ratio of amino acid to phosphonic acid compound which is employed can range from about 0.5:1 to about 1.5:1. The ratio is preferably held at or near 1:1 in order to minimize bis substitution on the nitrogen atom of the amino group and to thereby maximize monosubstitution. The reaction is preferably conducted at elevated temperatures of from about 20° C. to about 105° C. for a period sufficient to produce the desired quantity of end product (N-phosphonoalkylated amino acid), e.g., a period of time up to about 12 hours (preferably 2-8 hours).

In accordance with the present invention, a catalytically effective amount (e.g., from about 0.5% to about 10%, by weight of the amount of the reactants) of a polyamine catalyst which contains a high enough concentration of amine nitrogen to enhance the reaction is included in the reaction medium to promote the reaction. These polyamine materials are known in the art and can be synthesized as described in the Encyclopedia of Polymer Science and Technology, Vol. 10, pp. 616–621, e.g., polymerization of ethylene imine or by reaction of ammonia or amines with polyfunctional alkylating agents such as ethylene dichloride or epichlorohydrin. Representative polyalkylene polyamines, as described in U.S. Pat. No. 3,275,588, contain groupings of the formula $H_2N\text{-}(C_nH_{2n}NH)_a\text{-}H$ where n can be 2–4 and a can range from about 6–28 depending on the value of n. For example a can have a sufficient value to give a polymer having a molecular weight of 400–1200. The internal nitrogens in the chains of the above formula can be crosslinked with the nitrogens of other chains, e.g., by means of alkylene groups including $C_nH_{2n}$ where n is a positive integer as previously defined. The polyamine catalyst can contain primary, secondary, tertiary and/or quarternary amine structures. A representative material for use herein is a water soluble poly(ethylene amine) which is sold under the trademark PURIFLOC C-31 by Dow Chemical. In general, the amine nitrogens contained in the polyamine catalyst should be separated from one another by no more than about four atoms so that the amine groups are close enough to effectively bind the acid coreactants or their anions in order to promote the reaction.

The following Examples illustrate further embodiments of the present invention.

COMPARATIVE EXAMPLE 1

Chloromethylphosphonic acid (40.5 gm; 0.3 mole) and glycine (22.5 gm; 0.3 mole) were added to a 250 ml., three neck flask equipped with a mechanical stirrer, thermometer, pH probe, condenser, addition funnel, $N_2$ purge and heating mantle. Then 72 gm of a 50% aqueous sodium hydroxide solution was added at 40°–45° C. dropwise. The temperature was then raised to 80° C. In order to maintain the pH of the reaction medium in the range of approximately 9.5–10.5, 15 gm more of an aqueous sodium hydroxide solution (50%) was gradually added while the temperature was maintained at 90° C. for about 13 hours.

The reaction flask was then allowed to cool to 20° C., and 70 ml. of concentrated HCl was added to bring the pH to 1.5. A two phase system resulted with a white precipitate on the bottom and an amber liquid on the top. The pH was adjusted to 3.2 by addition of 50% sodium hydroxide. The precipitate remaining in the flask was filtered and washed with water and weighed 19 gm. The filtrate had a weight of 240 gm. It was found by analysis that the solid did not contain any glyphosate but that all the glyphosate product was in the filtrate. The filtrate contained 16.6 gm of glyphosate by high pressure liquid chromatography (HPLC) analysis. The yield of glyphosate was therefore 40.4%. There was also 31.7 gm of glyphosine based upon $^{31}$P nmr analysis which amounts to a 43.3% yield based on the amount of phosphonic acid used.

EXAMPLE 2

This represents a repetition of Comparative Example 1 with the exception that a polyalkylene polyamine catalyst (PURIFLOC C-31 brand from Dow Chemical Corporation) was used to enhance the yield of product. The same amounts of chloromethylphosphonic acid, glycine and sodium hydroxide used in the previous Example were employed and the same experimental procedure was used. To the reaction mixture was added 1.0 gm. of the polyquaternary catalyst before the sodium hydroxide solution had been gradually added for pH adjustment. The yield of precipitate was only 3 gm. It did not contain glyphosate. The filtrate after acidification had a weight of 266 gm. and by HPLC analysis was found to contain 23.7 gm of glyphosate for a 57.6% yield. An nmr analysis showed glyphosine was also present but in lesser amount than in Example 1.

EXAMPLE 3

This represents a two-fold scale up of the above Example 2. An nmr analysis showed a 55% yield of glyphosate and less glyphosine than in Example 1.

COMPARATIVE EXAMPLE 4

This Example illustrates the results that were obtained when a poly(amine/amide) material is used in which the amine nitrogens are separated from one another by the amide groups by substantially more than about 4 atoms (i.e., about 9–10 atoms).

The reaction was conducted in a 500 ml. round bottom flask with stirrer, condenser, thermometer and dropping funnel. The flask was charged with 50 ml. of water and 45 gm. (0.60 mole) of glycine which was brought to a pH of 9 by the addition of 50% sodium hydroxide solution. Then 3 gm. of polyquaternary ammonium halide made from a polyacrylamide by the Mannich reaction with formaldehyde and dimethyl amine followed by quaternization with methyl chloride was added. This material is commercially available under the trademark PURIFLOC C-43 from Dow Chemical. The solution was stirred at 89° C. while a solution of 81 gm. of chloromethylphosphonic acid (0.60 mole) in 70 ml. of water brought to a pH of 7 by the addition of 50% sodium hydroxide was added over a period of five hours. The pH was maintained at 9.5–10.5 over a period of six hours by the addition of 50% sodium hydroxide. The solution was then acidified and analyzed. The glyphosate yield was only about 8.3%. Considerable unreacted chloromethylphosphonic acid was present. The glyphosine yield was about 3%.

The foregoing Examples have merely been given to illustrate certain preferred embodiments of the present invention and should not, therefore, be construed in a limiting sense. The scope of protection which is sought is set forth in the claims which follow.

As used herein the terms "amino acid" and "haloalkylphosphonic acid" are intended to cover not only the free acid species but also the salts thereof (e.g., alkali metal and ammonium) which can be used to perform the desired reaction. Similarly, the term "phosphonoalkylated amino acid" is intended to cover the corresponding product formed thereby whether the reactants are in the free acid or salt form, or partially in each of these forms.

What is claimed:

1. In the process for forming N-phosphonoalkylated amino acids by reaction of an amino acid, $HO_2CRNH_2$, with R alkylene, with a haloalkylphosphonic acid, wherein the improvement consists of using a catalytically effective amount of a polyamine catalyst which comprises groupings of the formula $H_2N-(C_nH_{2n}NH)_a-H$ where n can be 2 to 4 and a can range from 6 to 28 which contains a sufficiently high concentration of amine nitrogen atoms to promote the reaction.

2. A process as claimed in claim 1 wherein the amino acid has the formula $HO_2CRNH_2$ where R is an unsubstituted or substituted alkylene group of 1 to about 10 carbon atoms in its backbone.

3. A process as claimed in claim 1 wherein the haloalkylphosphonic acid has the formula $XRP(O)(OH)_2$ where X is chlorine and R is an unsubstituted or substituted alkylene group of 1 to about 10 carbon atoms in its backbone.

4. A process as claimed in claim 1 wherein the amount of catalyst ranges from about 0.5% to about 10%, by weight of the reactants.

5. A process as claimed in claim 2 wherein the amount of catalyst ranges from about 0.5% to about 10%, by weight of the reactants.

6. A process as claimed in claim 3 wherein the amount of catalyst ranges from about 0.5% to about 10%, by weight of the reactants.

7. A process as claimed in claim 1 wherein the amino acid has the formula $HO_2CRNH_2$ where R is methylene, the haloalkylphosphonic acid has the formula $XCH_2P(O)(OH)_2$ where X is chlorine, and the polyamine catalyst is present at from about 0.5% to about 10%, by weight of the reactants.

8. A process as claimed in claim 1 where the reaction is conducted at a pH of from about 8.5 to about 12.5.

9. A process as claimed in claim 7 wherein the reaction is conducted at a pH of from about 9.5 to about 10.5.

* * * * *